(12) United States Patent
Sembritzki

(10) Patent No.: US 6,986,604 B2
(45) Date of Patent: Jan. 17, 2006

(54) METHOD FOR DETERMINING AND LOCATING MEASUREMENT SYSTEM ERRORS IN COMPUTED TOMOGRAPHY CAUSED BY INTERFERING OBJECTS

(75) Inventor: Otto Sembritzki, Wachenroth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/927,148

(22) Filed: Aug. 27, 2004

(65) Prior Publication Data

US 2005/0047553 A1    Mar. 3, 2005

(30) Foreign Application Priority Data

Aug. 27, 2003  (DE)  ................................ 103 39 486

(51) Int. Cl.
*G01D 18/00*    (2006.01)
(52) U.S. Cl. ............................ 378/207; 378/4; 378/145
(58) Field of Classification Search ................ 378/207, 378/4, 19, 119, 134, 145, 901; 250/252.1, 250/363.01, 493.1; 382/131
See application file for complete search history.

(56) References Cited

U.S. PATENT DOCUMENTS

| | | | |
|---|---|---|---|
| 2002/0165686 A1 * | 11/2002 | Kropfeld et al. | ............. 702/104 |
| 2003/0219092 A1 * | 11/2003 | Bressel et al. | ................. 378/4 |
| 2004/0022364 A1 * | 2/2004 | Stierstorfer et al. | ........ 378/207 |

* cited by examiner

*Primary Examiner*—Edward J. Glick
*Assistant Examiner*—Irakli Kiknadze
(74) *Attorney, Agent, or Firm*—Harness, Dickey & Pierce P.L.C.

(57) ABSTRACT

A method is for determining a position of an object causing interference in the beam path of a computed tomography unit. The method includes recording a first calibration table in a first moving focal point mode and recording a second calibration table in a second moving focal point mode. The method further includes creating two differential tables based on the first and second calibration tables, each with a corresponding already available calibration table recorded in the same moving focal point mode and in interference-free operation. Finally, the position of the object causing the interference in the beam path is determined, based on the differential tables.

16 Claims, 2 Drawing Sheets

METHOD FOR DETERMINING AND LOCATING MEASUREMENT SYSTEM ERRORS IN COMPUTED TOMOGRAPHY CAUSED BY INTERFERING OBJECTS

The present application hereby claims priority under 35 U.S.C. §119 on German patent application number DE 103 39 486.9 filed Aug. 27, 2003, the entire contents of which are hereby incorporated herein by reference.

FIELD OF THE INVENTION

The present invention generally relates to computed tomography, as used in medicine to examine patients. The present invention thereby relates in particular to a method for simplifying or improving error analysis in measurement systems in CT units.

BACKGROUND OF THE INVENTION

Modern medical diagnostic methods, such as x-ray computed tomography (CT), can be used to obtain image data of a measurement object to be examined. The measurement objects examined are generally patients.

X-ray computed tomography—hereafter abbreviated to CT—is a specific x-ray imaging method, which differs in principle from conventional x-ray layer imaging methods in the structure of the image. With CT imaging systems transverse sectional images are obtained, in other words layers of the body are mapped essentially perpendicular to the axis of the body. The tissue-specific physical variable shown in the image is the distribution of the attenuation value of x-ray radiation $\mu(x,y)$ in the sectional plane. The CT image is obtained by reconstructing the one-dimensional projections of the two-dimensional distribution of $\mu(x,y)$ supplied by the measurement system used from very many different angles.

The projection data is determined from the intensity I of an x-ray beam after it has passed through the layer to be mapped and from its original intensity $I_0$ at the x-ray source according to the absorption law $$\ln\frac{I_o}{I} = \int_L \mu(x,y)dl$$

The integration path L represents the route of the x-ray beam in question through the two-dimensional attenuation distribution $\mu(x, y)$. An image projection is then composed from the measurement values of the line integrals through the object layer obtained with the x-ray beams in one direction.

Projections from the widest range of directions—characterized by the projection angle α—are obtained by use of a combined x-ray tube detector system, which rotates about the object in the plane of the layer. The most commonly used devices at present are what are known as "fan beam devices", in which a tube and an array of detectors (a linear arrangement of detectors) rotate together in the plane of the layer about a center of rotation, which is also the center of the circular measurement field. "Parallel beam devices", which have very long measuring times, are not described here. It should however be pointed out that it is possible to transform fans to parallel projections and vice versa, so the present invention, which will be described with reference to a fan beam device, can also be used without restriction for parallel beam devices.

Generally errors can occur in the measurement system of a CT unit. The measurement system includes the x-ray radiation source (tube), the tube-side diaphragms to collimate the x-ray beam fan and the detector. In the case of modern CT units the detector generally includes ceramic detector elements and a downstream electronics system for signal preparation (integration and amplification) and for analog-digital conversion. Errors with different causes in the measurement system can be discerned in the subsequently reconstructed CT image by interference from, for example, annular image artifacts, which from a diagnostic point of view alone have to be suppressed—in order to prevent misdiagnosis. It is therefore necessary to determine the error source, during service operations in particular.

Until now in the prior art it was necessary to record specific measurement data in additional scans, for example to exclude the detector as an error source, with the measured data being stored on data media and sent to the detector manufacturer for analysis (generally not electronically). There is as yet no method for verifying the functionality of the x-ray source. If a tube error is suspected, the tube has to be replaced, taken apart and examined mechanically.

Such a procedure is both time-consuming and cost-intensive.

SUMMARY OF THE INVENTION

An object of an embodiment of the present invention is to provide a method. In particular, the method may be one which determines error sources in the region of the tubes—specifically between the focal point and outer facing in the exit region—without major expenditure.

According to an embodiment of the invention, a method is for determining and locating an object causing interference in the beam path of a computed tomography device, comprising the following stages:

Recording of a first calibration table in a first moving focal point mode,

Recording of a second calibration table in a second moving focal point mode,

Creation of two differential tables based on the first and second calibration tables, each with a corresponding already available calibration table recorded in the same moving focal point mode and in interference-free operation, and Determination of the position of the object causing the interference in the beam path based on the differential tables.

The position of the object may thereby advantageously be determined in a linked representation of both differential tables based on the horizontal distance between two extremal points caused by the interference and above a minimum value.

Also in one advantageous embodiment of the inventive method, the recording of calibration tables and the comparison for analysis purposes of the resulting differential tables with interference-free calibration tables are carried out routinely during standard operation of the CT unit between patient measurements.

In one embodiment, a device is created for implementing a method according to one of the embodiments mentioned.

BRIEF DESCRIPTION OF THE DRAWINGS

Further advantages, features and characteristics of the present invention are described in more detail below based on exemplary embodiments with reference to the accompanying drawings, in which.

DETAILED DESCRIPTION OF THE PREFERRED EMBODIMENTS OF THE INVENTION

Figure 1:
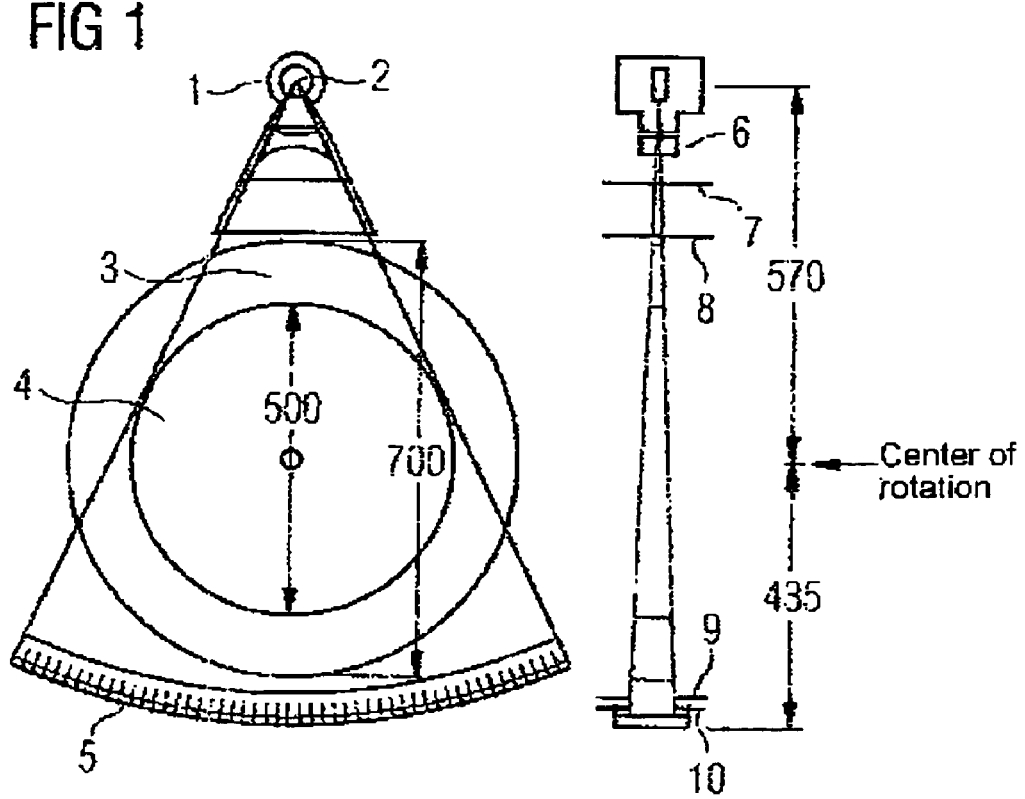
FIG. 1 shows a schematic illustration of the recording geometry and components of a CT measurement system from above (x-y plane) and from the side (y-z plane)

A CT unit may include different collimators, diaphragms, filters and screens or seals, which filter the x-ray spectrum, define the image layer, screen the detector from radiation leakage and protect against radiation as well as preventing the penetration of foreign bodies into the tube. FIG. 1 shows components of the measurement system of a CT unit from above and from the side.

The focal point 2 of the x-ray tube 1 determines the exit point of the fan beam. A first rough fading-in operation takes place in a first stage near to the focal point via a form filter 6, to reduce the emitted beam cone to the maximum beam fan necessary for the respective detector 5. In a second stage the maximum permitted fan is defined precisely by way of a fixed diaphragm 7. An additional adjustable diaphragm 8 allows variable fading-in to the respectively required layer thicknesses. Layer width and layer profile are thereby determined by focal width, filter and diaphragm geometry. The layer profile is also favorably influenced by the use of a detector-side movable diaphragm 9 and a detector-side fixed diaphragm 10. In order to prevent the penetration of foreign bodies (for example contrast agents) into the tube-side beam path, there is a sealing strip made of Plexiglas directly in front of the adjustable diaphragms 8 and 9.

However it is possible for a foreign body (splinter, oil droplet, contrast agent, etc.) to enter the measurement system (tube-side or detector-side) either during manufacture or during operation. If such a foreign body enters the beam path (for example due to rotation of the measurement system), it can represent an interfering object in that it in an unfavorable instance it can influence the signal level by its attenuation. "Unfavorable instance" here means that the interfering element in the beam path either changes position during rotation of the measurement system or the attenuation characteristic of the interfering element changes in the same position. The first instance—the alternating presence and absence—represents the most common error, in which for example a splinter moves around inside the cavity of the tube, entering the beam path now and then. The second instance can occur for example when a droplet of oil or contrast agent in the x-ray tube changes shape as it becomes warmer.

Normally, if the interfering object does not change its position or attenuation characteristic during the complete rotation of the measurement system (360° rotation), the attenuation is not discernable in the reconstructed CT image (in the form of image artifacts), as the attenuation is equally visible in all projections. Only one variation in the measurement data during rotation—with or without patient (absorber)—leads to corresponding mapping and therefore image errors after image reconstruction.

The inventive method involves identifying the interfering element, ultimately by detecting its position in relation to the focal point. To do this the inventive method uses the calibration tables supplied with the overall CT system by the detector manufacturer, which on the one hand contain the differences between the individual detector elements, on the basis of which the detector array was calibrated, and which on the other hand are intended to document the correct and error-free operation of the measurement system, in particular the detector array. Such calibration tables are generally determined before delivery of the CT system, by taking a total of 1000 projection measurements at an azimuth projection interval of 36° in moving focal point mode without an absorber (without patients). The calibration tables are generally available in the CT storage and computer units.

Figure 2:
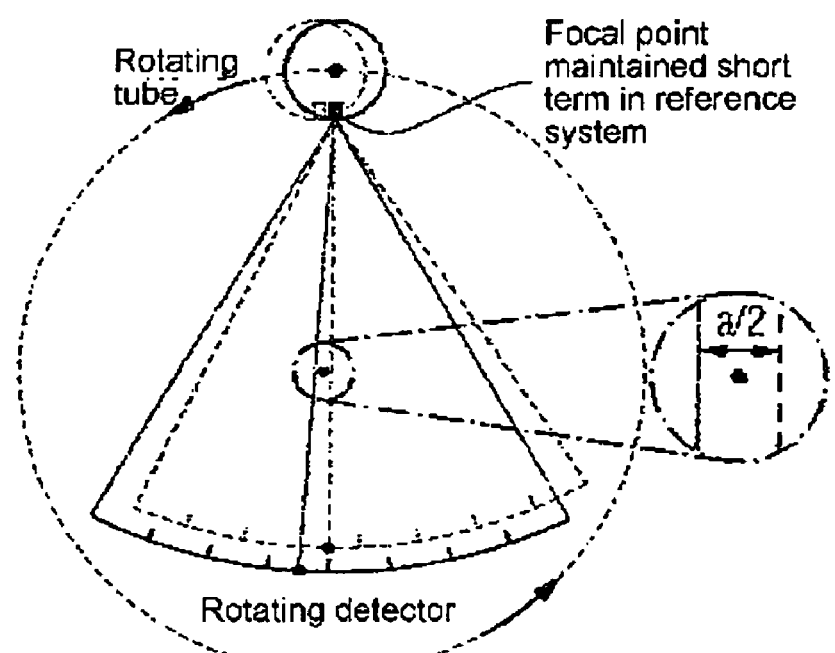
FIG. 2 shows a CT tube detector system in moving focal point mode.

Moving focal point mode (mode of operation is shown in FIG. 2) means that the focal point on the anode integrated in the x-ray tube is displaced counter to the direction of movement of the tube and therefore remains stationary within the reference system of the chamber during the time taken for two successive measurements. The focal point then moves back in an electromagnetically controlled manner to its original position on the anode and the process is repeated. As the detector moves on continuously, this method means that for every focal point position within the reference system of the chamber there are two measured projections, offset within each other by a/2 (detector width a). The purpose of the moving focal point mode is to double the scan speed, thereby enhancing local resolution.

The 1000 projection measurements spread respectively over ten projections therefore provide a total of 20 calibration tables in moving focal point mode, whereby for each one 50 measurement values are determined per channel (per detector element). Generally the two calibration tables, each of which is associated with one focal point position, are combined in one diagram.

Figure 3A:
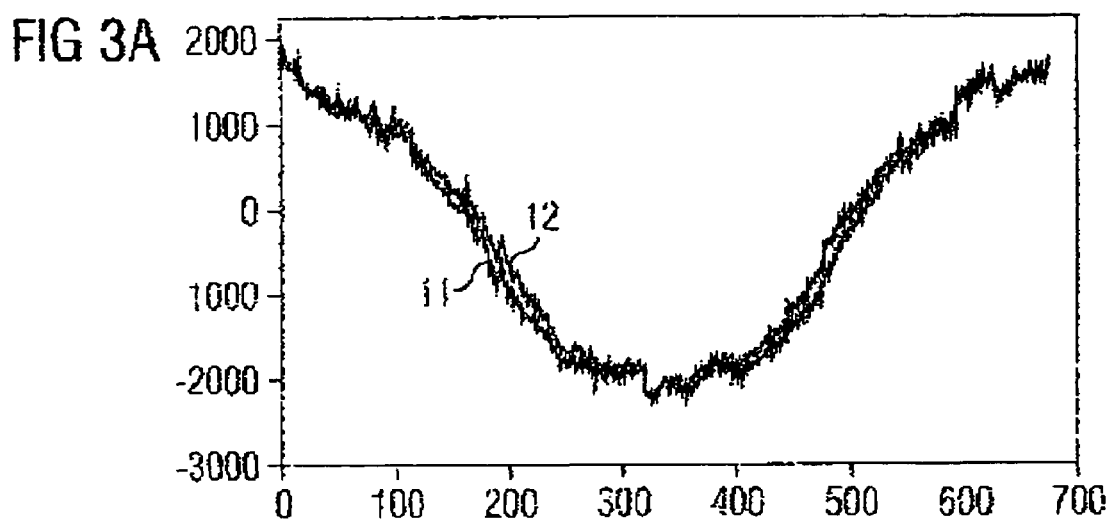
FIG. 3a shows two calibration tables affected by interference, each of which was acquired at different moving focal point positions.

Such a diagram, containing a first 11 and a second 12 calibration table according to a respective single focal point position, is shown in FIG. 3a. It shows 672 measured channels, which were measured (twice) at one time—possibly before delivery of the CT unit—when there were no interfering elements in the beam path. Such calibration tables are referred to during the further course of the description as basic calibration tables, as they are used in the context of the present invention for comparison with calibration tables affected by interfering elements.

Figure 3B:
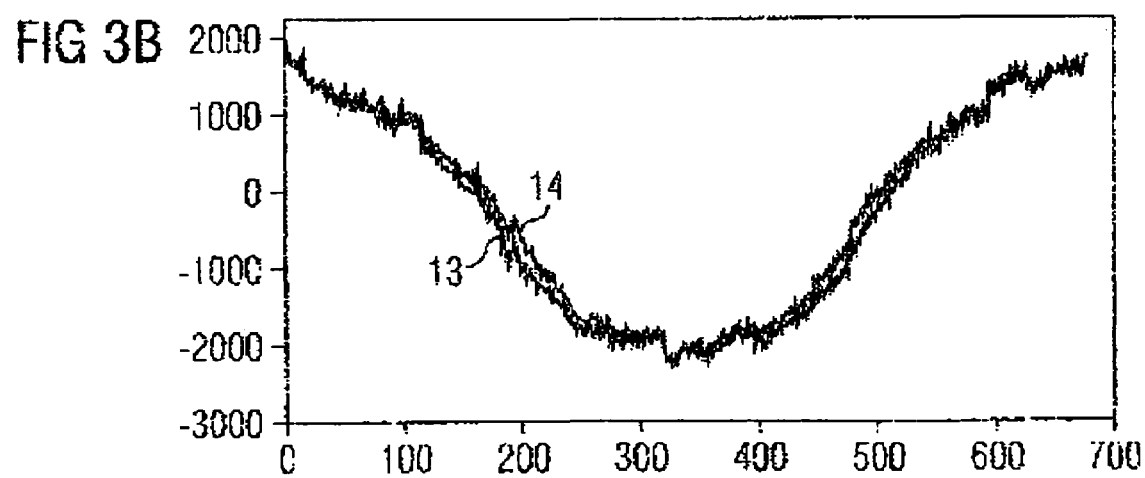
FIG. 3b shows two interference-free calibration tables, each of which was acquired at different moving focal point positions.
Figure 3C:
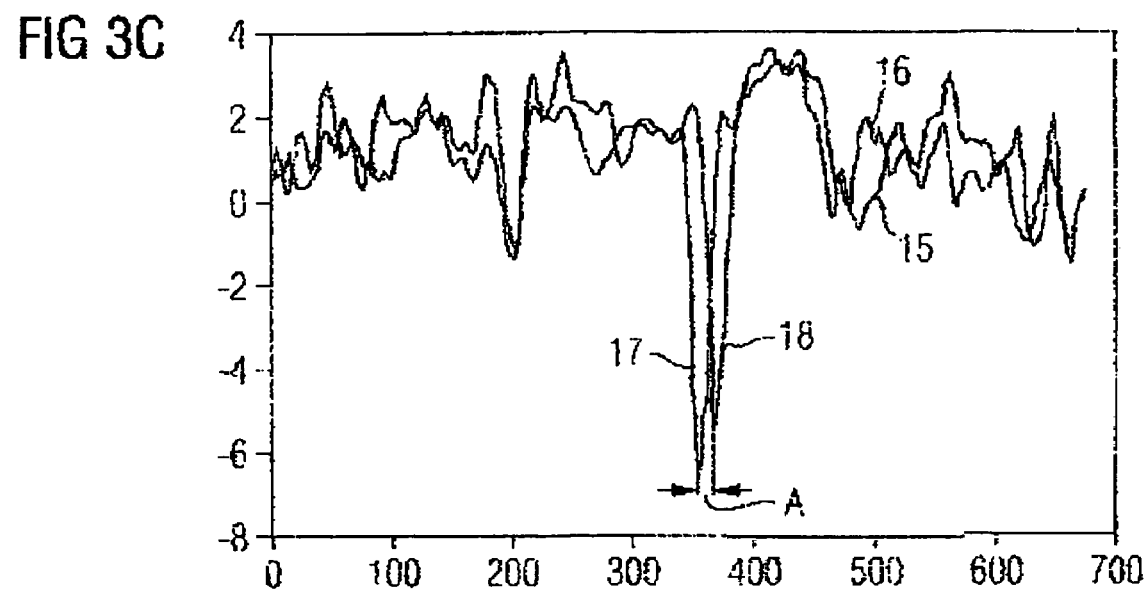
FIG. 3c shows a differential table, which was created on the basis of the first and second calibration tables affected by interference, each of which was created with an already available interference-free calibration table recorded in the correspondingly identical moving focal point mode.

Calibration tables affected by interfering elements are shown in FIG. 3b, i.e. calibration table 13 and calibration table 14 were recorded when there was an interfering element in the beam path or after annular artifacts became visible in the image. The basic focal point position of the diagram in FIG. 3b is the same as the one in the diagram in FIG. 3a, so both diagrams can be compared directly with each other. The calibration tables in both diagrams appear identical. Only the representation of the differences between the respective calibration tables in a differentiation diagram (FIG. 3c: |Calibration table 12–Calibration table 14|; |Calibration table 11–Calibration table 13|) shows a clear difference: between channel number 300 and 400 two clear extremal points 17,18 can be identified, which are due to different mapping positions of an interference body in the beam path.

Both extremal points (in this case minima) are due to signal attenuation in calibration tables 13 and 14 caused by the interfering elements. The horizontal distance between both extremal points A is in this instance approx. 13 units (units specified in channel numbers). The horizontal displacement or distance between both extremal points is due to the movement of the focal point due to moving focal point mode: as during moving focal point mode of a CT unit the focal point is maintained in stages counter to the direction of movement of the tube, an object in the beam path will be mapped at a different point on the detector array after displacement of the focal point compared with before displacement.

The radial distance of the interfering element from the focal point can be determined from this displacement on the detector array on the basis of the mapping formula, which can be written mathematically using a beam set.

Three characteristic distances can occur:
1. Distance of focal point 2 from form filter 6,
2. Distance of focal point 2 from adjustable tube-side diaphragm 8,
3. Distance of focal point 2 from adjustable detector-side diaphragm 9.

If the distance between the interfering object and the focal point corresponds to one of the three characteristic distances 1., 2. or 3. based on the differential diagram, the position of the interfering object in the measurement system is identified. In instance 1., i.e. where the interfering object is suspended on or in the form filter 9, the tube-side measurement system generally has to be sent in to have the form filter changed or cleaned. In instances 2. or 3., i.e. where the interfering object is on one of the two adjustable diaphragms 8 or 9, these can be changed without major technical effort and the error thus eliminated.

An exemplary embodiment of the implementation of the inventive method in or on a CT unit is summarized below:

A) If annular artifacts occur in the reconstructed image, two sets of calibration tables are measured and stored in the CT computer in moving focal point mode on the user's initiative.
B) Also on the initiative of the user or automatically immediately after this set of calibration tables has been measured, these two sets of calibration tables are compared mathematically with the interference-free basic calibration tables supplied by the manufacturer of the measurement system and available on the CT computer, in that for example a differential table is created by the CT computer by the use of differential formation.
C) In the event of the presence over time of a significant interfering object in the beam path of the CT measurement system, significant extreme values occur in the differential table, the horizontal distance between which (distance in detector units) is determined mathematically either by the CT computer automatically or by the user by a mouse click. The CT computer can determine the radial position of the interfering element in the beam path (in relation to the focal point) based on this distance value and the known geometry of the measurement system.

At least one embodiment of the inventive method thereby allows fast and uncomplicated location of an interfering object present in the measurement system, so that in the most favorable instance the interference can be eliminated in the simplest manner—i.e. by replacing a measurement system component (for example one of the two adjustable diaphragms).

At least one embodiment of the inventive method is based on available (basic) calibration tables or such tables acquired during the interference-free operation of the CT unit, which are compared easily with calibration tables affected by interference. Measuring calibration tables of any type (affected by interference or interference-free) is uncomplicated and involves a level of time and effort which cannot be compared with that of storing the raw data, sending the data medium containing the raw data to the detector manufacturer and its analysis according to the prior art.

Therefore the measurement of calibration tables affected by interference and/or interference-free calibration tables and their comparison in the context of a software-assisted analysis can be carried out during the actual measurement operation, when there is no absorber (patient) present in the measurement image. If the signal attenuation due to interfering objects exceeds a tolerance threshold, in one advantageous embodiment of the invention a warning message is output, which also indicates the defective (measurement) system component. If the error analysis does not identify the defective component, it would be possible to transmit the calibration tables affected by interference electronically to the detector manufacturer quickly and easily so that a more precise examination of the interference can be undertaken there.

Any of the aforementioned methods may be embodied in the form of a program. The program may be stored on a computer readable media and is adapted to perform any one of the aforementioned methods when run on a computer. Thus, the storage medium or computer readable medium, is adapted to store information and is adapted to interact with a data processing facility or computer to perform the method of any of the above mentioned embodiments.

The storage medium may be a built-in medium installed inside a computer main body or removable medium arranged so that it can be separated from the computer main body. Examples of the built-in medium include, but are not limited to, rewriteable involatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable involatile memory, such as memory cards; and media with a built-in ROM, such as ROM cassettes.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. Method for determining a position of an object causing interference in an X-ray beam path of a computed tomography unit, comprising:
   recording a first calibration table in a first moving focal point mode;
   recording a second calibration table in a second moving focal point mode;
   creating two differential tables based on the first and second calibration tables, each with a corresponding already available calibration table recorded in the same moving focal point mode and in interference-free operation; and
   determining the position of the object causing the interference in the X-ray beam path, based on the differential tables.

2. Method according to claim 1, wherein the position of the object is determined in a linked representation of both differential tables based on the horizontal distance between two extremal points caused by the interference and above a minimum value.

3. A program, said program comprising instructions to perform the method of claim 2, when executed on a computer.

4. A computer readable medium, said medium storing the program of claim 3.

5. Method according to claim 1, wherein the recording of calibration tables and the comparison for analysis purposes of the resulting differential tables with interference-free calibration tables is carried out routinely during standard operation of the CT unit between patient measurements.

6. A program, said program comprising instructions to perform the method of claim 5, when executed on a computer.

7. A computer readable medium, said medium storing the program of claim 6.

8. Method according to claim 1, wherein the recording of calibration tables and the comparison for analysis purposes of the resulting differential tables with interference-free calibration tables is carried out routinely during standard operation of the CT unit between patient measurements.

9. A program, said program comprising instructions to perform the method of claim 8, when executed on a computer.

10. A computer readable medium, said medium storing the program of claim 9.

11. A program, said program comprising instructions to perform the method of claim 1, when executed on a computer.

12. A computer readable medium, said medium storing the program of claim 11.

13. An apparatus for determining a position of an object causing interference in an X-ray beam path of a computed tomography unit, comprising:

means for recording a first calibration table in a first moving focal point mode and for recording a second calibration table in a second moving focal point mode;

means for creating two differential tables based on the first and second calibration tables, each with a corresponding already available calibration table recorded in the same moving focal point mode and in interference-free operation; and means for determining the position of the object causing the interference in the X-ray beam path, based on the differential tables.

14. The apparatus according to claim 13, wherein the position of the object is determined in a linked representation of both differential tables based on the horizontal distance between two extremal points caused by the interference and above a minimum value.

15. The apparatus according to claim 14, wherein the recording of calibration tables and the comparison for analysis purposes of the resulting differential tables with interference-free calibration tables is carried out routinely during standard operation of the CT unit between patient measurements.

16. The apparatus according to claim 13, wherein the recording of calibration tables and the comparison for analysis purposes of the resulting differential tables with interference-free calibration tables is carried out routinely during standard operation of the CT unit between patient measurements.

\* \* \* \* \*